US012376840B2

(12) United States Patent
Liu et al.

(10) Patent No.: US 12,376,840 B2
(45) Date of Patent: *Aug. 5, 2025

(54) OCCLUDER PUSHING DEVICE AND TRANSPORT SYSTEM

(71) Applicant: Lifetech Scientific (Shenzhen) Co., Ltd., Shenzhen (CN)

(72) Inventors: Xiangdong Liu, Shenzhen (CN); Xianmiao Chen, Shenzhen (CN); Mingjuan Fu, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 368 days.

This patent is subject to a terminal disclaimer.

(21) Appl. No.: 17/879,534

(22) Filed: Aug. 2, 2022

(65) Prior Publication Data
US 2022/0361864 A1 Nov. 17, 2022

Related U.S. Application Data

(63) Continuation of application No. 16/629,112, filed on Jan. 7, 2020, now Pat. No. 11,419,591.

(51) Int. Cl.
*A61B 17/00* (2006.01)
*A61B 17/12* (2006.01)

(52) U.S. Cl.
CPC .... *A61B 17/0057* (2013.01); *A61B 17/12122* (2013.01); *A61B 2017/00592* (2013.01);
(Continued)

(58) Field of Classification Search
CPC .......... A61B 17/0057; A61B 17/12022; A61B 17/12109; A61B 17/12122;
(Continued)

(56) References Cited

U.S. PATENT DOCUMENTS 11,419,591 B2 * 8/2022 Liu .................. A61B 17/12022
2018/0279994 A1 * 10/2018 Schaer ..................... A61B 8/12

* cited by examiner

*Primary Examiner* — Mohamed G Gabr
(74) *Attorney, Agent, or Firm* — Raymond Sun

(57) ABSTRACT

The present disclosure relates to an occluder pushing device and an occluder delivery system, wherein the pushing device includes a pushing component and a handle. The pushing component includes a pushing tube and a traction element slidably inserted into the pushing tube. The handle is fixedly connected to a proximal end of the pushing tube and internally provided with a moving component and a locking component. The moving component includes a translation mechanism and a rotation mechanism, where the translation mechanism is used to drive the traction element to move axially inside the pushing tube, and the rotation mechanism is used to drive the traction element to rotate axially inside the pushing tube. The locking component is used to lock relative positions of the traction element and the pushing tube, and the rotation mechanism includes a locking structure for locking or releasing linkage between the rotation mechanism and the traction element. The pushing device of the present invention has provided therein the locking component for locking the traction element and the pushing tube in relative positions, such that when the pushing tube pushes the occluder, the relative positions of the traction element and the pushing tube lock the occluder in a folded state, thereby preventing the occluder from being prematurely released before reaching a pre-determined position.

20 Claims, 13 Drawing Sheets

(52) U.S. Cl.
CPC ............... *A61B 2017/00623* (2013.01); *A61B 2017/1205* (2013.01); *A61B 17/12109* (2013.01)

(58) Field of Classification Search
CPC .. A61B 2017/0053; A61B 2017/00575; A61B 2017/00592; A61B 2017/00606; A61B 2017/00623; A61B 2017/1205; A61B 2017/12095
See application file for complete search history.

OCCLUDER PUSHING DEVICE AND TRANSPORT SYSTEM

TECHNICAL FIELD

The present disclosure belongs to the technical field of interventional medical devices, and relates to an occluder pushing device and a delivery system including the same.

BACKGROUND ART

The use of interventional methods for the treatment of cardiovascular diseases by catheter technology is currently the commonly used treatment. Specifically, various materials, devices and the like are placed in the heart, arteries, venous vessels and other parts of a human body through interventional catheter techniques for the treatment of the cardiovascular diseases.

For example, interventional medical devices, such as an atrial septal defect (ASD) occluder, a ventricular septal defect (VSD) occluder, a patent ductus arteriosus (PDA) occluder, a patent foramen ovale (PFO) occluder, etc., are delivered through a catheter interventional method, to reach a defect location of the heart to occlude the defect for treating a congenital heart disease.

When the above-described interventional medical devices are delivered into the heart, the artery, the vein blood vessel, the left atrial appendage and the bronchus of the lungs of a human body through a delivery system, the interventional medical devices are usually pushed to a preset location through a flexible pushing component, then the interventional medical devices are released after the interventional medical devices and the pushing component are disconnected, and radiography or ultrasonography is used to confirm whether released position of the interventional medical devices is proper or not, whether the interventional medical instruments are unfolded or not, and whether the operation effect is satisfactory or not.

In the prior art, during an interventional medical operation, it is possible for the pushing device easily release the occluder in advance due to accidental contact, resulting an inaccurate release position which causes the operation to fail.

SUMMARY OF THE DISCLOSURE

Therefore, it is necessary to provide an occluder pushing device and a delivery system to solve the problem that the existing occluder pushing device can cause an inaccurate release position due to accidental contact.

In one aspect, the present disclosure provides an occluder pushing device, including:
a pushing component including a pushing tube and a traction element slidably inserted into the pushing tube; and
a handle fixedly connected with a proximal end of the pushing tube and internally provided with a moving component and a locking component, wherein
the moving component includes a translation mechanism and a rotation mechanism, the translation mechanism is configured to drive the traction element to move in an axial direction within the pushing tube, and the rotation mechanism is configured to drive the traction element to rotate around an axis within the pushing tube;
the locking component is configured to lock relative positions of the traction element and the pushing tube; and
the rotation mechanism includes a locking structure for locking or releasing linkage between the rotation mechanism and the traction element.

In one of the embodiments, the translation mechanism includes:
a first rotating element axially provided with a through hole through which the traction element penetrates;
a second rotating element coaxial with the first rotating element;
a linear guide rail and a balance sliding rail which are respectively provided on the first rotating element and the second rotating element and parallel to a rotation axis of the first rotating element; and
a horizontal driving component configured to drive a proximal end of the traction element to generate linear reciprocating motion along the linear guide rail and the balance sliding rail.

In one of the implementations, the horizontal driving component includes:
a traction element mounting seat slidably provided on the linear guide rail and the balance sliding rail, the proximal end of the traction element being fixed to the traction element mounting seat; and
a pushing part connected with the traction element mounting seat and at least partially exposed from the handle so as to push the traction element mounting seat to move along the linear guide rail and the balance sliding rail.

In one of the embodiments, the rotation mechanism is provided at an end of the second rotating element far from the first rotating element, and further includes:
a base, which is a hollow barrel and is fixed to a housing of the handle; and
an adjusting rod slidably inserted into the base and rotatably linked with the second rotating element;
where the structure is provided on the base and the adjusting rod, and has a locking state and an unlocking state to respectively restrain and release the rotational degree of freedom of the adjusting rod within the base; and
the locking structure may be in the locking state or the unlocking state by axially adjusting the relative positions of the adjusting rod and the base.

In one of the embodiments, a damping edge is provided on a surface of the balance sliding rail along a moving direction of the traction element mounting seat, and a sliding element which elastically abuts against the damping edge is provided in the traction element mounting seat.

In one of the embodiments, the pushing part is axially limited on the traction element mounting seat, and the first rotating element and the second rotating element transmit the traction element mounting seat to rotate around the rotation axis of the first rotating element relative to the pushing part through the linear guide rail and the balance sliding rail.

In one of the embodiments, the locking structure includes:
stopping pieces circumferentially provided at intervals around an inner side wall of the base;
stopping teeth circumferentially provided at intervals around an outer side wall of the adjusting rod, wherein tooth grooves are formed between the adjacent stopping teeth; and
an annular groove circumferentially formed around the inner side wall of the base, wherein when the adjusting rod rotates within the base, the stopping teeth rotate within the annular groove; and the stopping pieces may be clamped in the tooth grooves or the stopping teeth may be moved into the annular groove by axially adjusting the relative positions of the adjusting rod and the base.

In one of the embodiments, the traction element mounting seat and the pushing part are axially limited through a limiting edge and a limiting groove which are mutually aligned circumferentially, and the cross section of the limiting edge and the limiting groove at the matching position are circular to achieve the rotation of the traction element mounting seat relative to the pushing part.

In one of the embodiments, position clamping structures are provided on the inner side wall of the base and the outer side wall of the adjusting rod, so that the adjusting rod is axially limited in the base without interference of external force.

In one of the embodiments, the rotation mechanism further includes:
a rotary cover fixed at an end of the adjusting rod far from the second rotating element;
a spring seat surrounding the base; and
a spring elastically pressed between the spring seat and the rotary cover; and
the position clamping structure includes a clamping ring and a first clamping groove, wherein the clamping ring extends from the inner side wall of the base radially and abuts against the outer side wall of the adjusting rod; the first clamping groove is circumferentially formed around the outer side wall of the adjusting rod; and
when the clamping ring is buckled with the first clamping groove, and the stopping pieces are clamped in the tooth grooves.

In one of the embodiments, the position clamping structure further includes a second clamping groove, wherein the second clamping groove is circumferentially formed around the outer side wall of the adjusting rod; and
when the clamping ring is buckled with the second clamping groove, the stopping teeth are positioned in the annular groove.

In one of the embodiments, the locking component includes:
a fixing seat fixed in the handle;
a movable element, a pore is formed between the movable element and the fixing seat for the traction element passes through; and
an adjusting structure configured to adjust the pore between the movable element and the fixing seat so as to lock or release the traction element.

In one of the embodiments, the adjustment structure includes:
a sleeve surrounding the fixing seat and the movable element, wherein the diameter of the minimum inscribed circle of the projection of the sleeve on the cross section perpendicular to the axial direction is less than the diameter of the maximum circumscribed circle of the fixing seat and the movable element; and
a locking wheel axially limited in the handle and in threaded connection with the sleeve,
wherein a hub of the locking wheel is at least partially exposed from the handle to rotate the locking wheel to transmit the sleeve to move axially, so that the sleeve grips or releases the fixing seat and the movable element.

In one of the embodiments, a tapered blind hole is formed in the sleeve; a circular truncated cone is formed by the alignment of the movable element and the fixing seat, and positioned in the tapered blind hole; and an end of the sleeve far from the opening of the tapered blind hole is in threaded connection with the locking wheel through a screw.

Correspondingly, in another aspect, the present disclosure provides an occluder delivery system which includes the above-described occluder pushing device, and
a delivery sheath, which is a hollow tube, and the pushing tube of the pushing device is slidably inserted into the delivery sheath; and
a sheath core connected to a proximal end of the delivery sheath and configured to adjust a bending direction of the delivery sheath so that the pushing tube pushes the occluder to a defect to be occluded along the delivery sheath.

In one of the embodiments, the delivery system further includes a hemostatic valve, wherein a hollow guide sheath is detachably connected between the delivery sheath and the hemostatic valve, and an inner cavity of the guide sheath is communicated with an inner cavity of the delivery sheath and an inner cavity of the hemostatic valve.

In one of the embodiments, the delivery system further includes a preloader detachably connected to a distal end of the guide sheath, and the preloader includes a horn section, an interface section and a connecting section connected between the horn section and the interface section.

The above-described occluder pushing device and the delivery system have the beneficial effects that the locking component for locking the traction element and the pushing tube at the relative positions are provided in the occluder pushing device, so that when the occluder is pushed by the pushing tube, the relative positions of the traction element and the pushing tube may maintain the state of the occluder, thereby avoiding an inaccurate releasing position of the occluder due to accidentally touching the pushing device.

BRIEF DESCRIPTION OF THE DRAWINGS

In order to more clearly illustrate the embodiments of the present disclosure or the technical solutions in the prior art, the drawings used in the description of the embodiments or the prior art will be briefly described below. Obviously, the drawings depicted hereinafter are only some embodiments of the present disclosure, and a person skilled in the art would obtain drawings of other embodiments from the drawings herein without involving any inventive effort.

DETAILED DESCRIPTION OF THE DISCLOSURE

Figure 1:
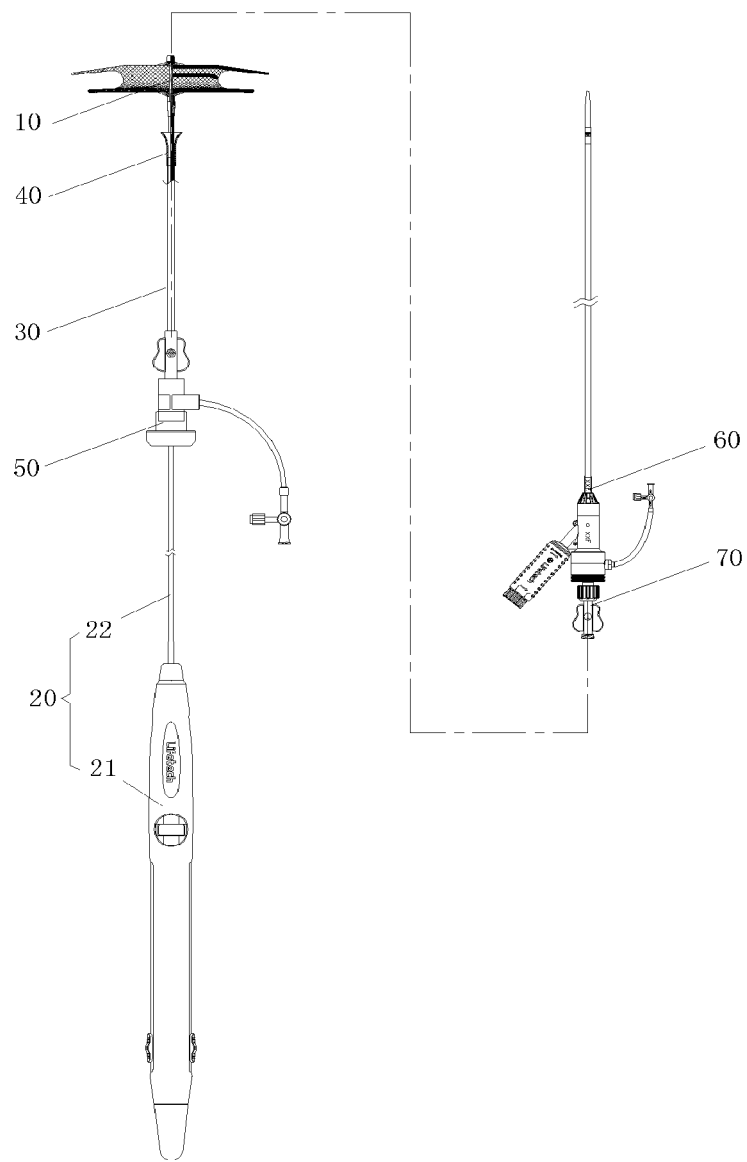
FIG. 1 is a schematic diagram of an occluder delivery system, in which a proximal end of a delivery sheath is connected to a distal end of a guide sheath after an occluder is received into the guide sheath by a preloader.

To facilitate an understanding of the present disclosure, the present disclosure will be described more fully hereinafter with reference to the accompanying drawings. Preferred implementations of the present disclosure are illustrated in the drawings. The present disclosure may, however, be embodied in many different forms and should not be construed as being limited to the implementations set forth herein. Rather, these implementations are provided so that the disclosure will be understood more thoroughly and completely.

It should be noted that the terms "distal end" and "proximal end" are used as terms of orientation commonly used in the field of interventional medical devices, where the "distal end" refers to the end far away from an operator during the operation and the "proximal end" refers to the end close to the operator during the operation. The axial direction refers to a direction parallel to the line connecting the center of the distal end and the center of the proximal end of the medical device; and the radial direction refers to a direction perpendicular to the axial direction.

Referring to FIGS. 1-4 and FIG. 5a, an occluder delivery system includes a pushing device 20, a delivery sheath 60, and a sheath core 70. The pushing device 20 includes a pushing component 22 and a handle 21. The pushing component 22 includes a pushing tube 221 and a traction element 222 slidably inserted inside the pushing tube 221; and the handle 21 is internally provided with a moving component and a locking component 214 which may lock the traction element 222 and the pushing tube 221 in relative positions. The moving component includes a translation mechanism 215 and a rotation mechanism 216, wherein the translation mechanism 215 is configured to drive the traction element 222 to move in an axial direction within the pushing tube 221; the rotation mechanism 216 is configured to drive the traction element 222 to rotate around an axis within the pushing tube 221; and the rotation mechanism 216 includes a locking structure for locking or releasing the linkage between the rotation mechanism 216 and the traction element 222. Thus, it is possible to prevent the situation where the rotation mechanism 216 drives the pulling element 222 to rotate around the axis within the pushing tube 221 due to accidental touching of the rotation mechanism 216 during the operation, thereby improving the operation accuracy of the pushing device 20.

Specifically, distal ends of the pushing tube 221 and the traction element 222 of the pushing component 22 are detachably connected to a proximal end and a distal end of the occluder 10, respectively, and the translation mechanism 215 enables the proximal end of the occluder 10 to be close to, or far away from, the distal end of the occluder 10 by controlling a relative position of the traction element 222 in the pushing tube 221 so as to unfold or fold the occluder 10. The locking component 214 locks the traction element 222 in a relative position with respect to the pushing tube 221 to prevent accidental touching of the pushing device 20 causing the traction element 222 to move along the pushing tube 221 to release the occluder 10 in advance.

Of course, it should be understood that in some embodiments, the delivery sheath 60 is a hollow tube and a bending direction of the delivery sheath 60 is adjusted by the sheath core 70 connected to a proximal end of the delivery sheath 60, so that the pushing tube 221 pushes the occluder 10 along the delivery sheath 60 to a defect to be occluded.

In some embodiments, the delivery system further includes a hemostatic valve 50, wherein a hollow guide sheath 30 is detachably connected between the delivery sheath 60 and the hemostatic valve 50, and an inner cavity of the guide sheath 30 is communicated with an inner cavity of the delivery sheath 60 and an inner cavity of the hemostatic valve 50, such that the occluder 10 is pushed by the delivery sheath 60 after the folded occluder 10 is received into the guide sheath 30 in advance.

Figure 23:
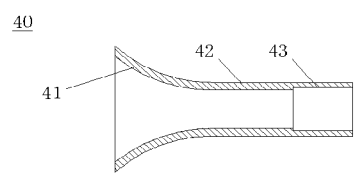
FIG. 23 is a structural schematic diagram of the preloader.
Figure 24:
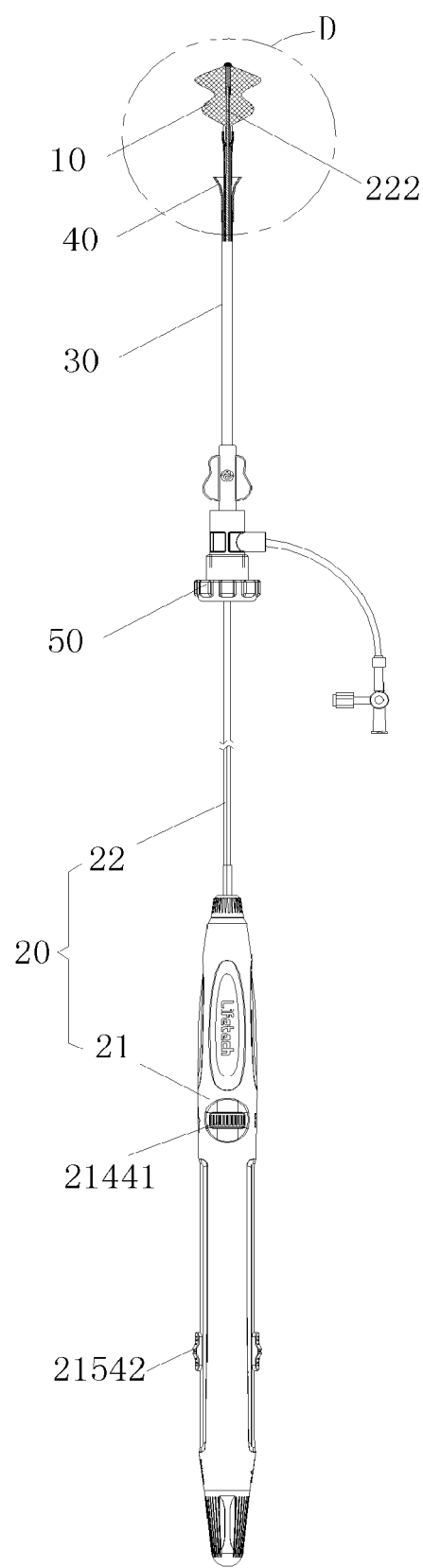
FIG. 24 is a state diagram of the occluder during the operation of the pushing device.

Referring also to FIGS. 1 and 24, in some embodiments, a preloader 40 is detachably connected to a distal end of the guide sheath 30. Referring to FIG. 23, the preloader 40 includes a horn section 41, an interface section 43 and a connecting section 42 connected between the horn section 41 and the interface section 43. The horn section 41 is formed with a large outwardly-extending opening to receive the occluder 10 into the guide sheath 30 by pulling the pushing component 22. It will be understood that the manner in which the interface section 43 is detachably connected with the guide sheath 30 is through a threaded connection or a buckle connection, such that after the occluder 10 is received in the guide sheath 30, the preloader 40 is removed and the proximal end of the delivery sheath 60 is connected to the distal end of the guide sheath 30.

Figure 2:
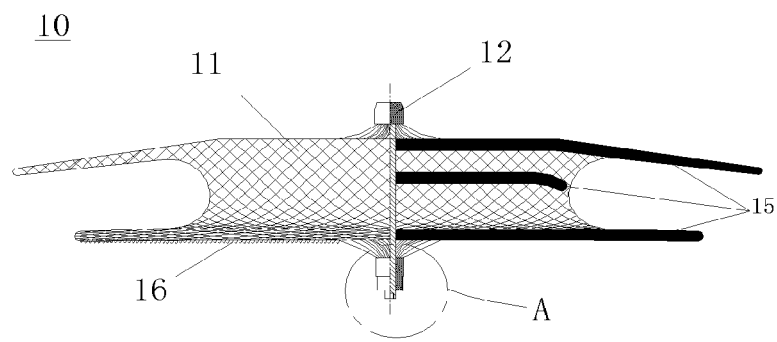
FIG. 2 is a structural schematic diagram of an occluder.
Figure 3:
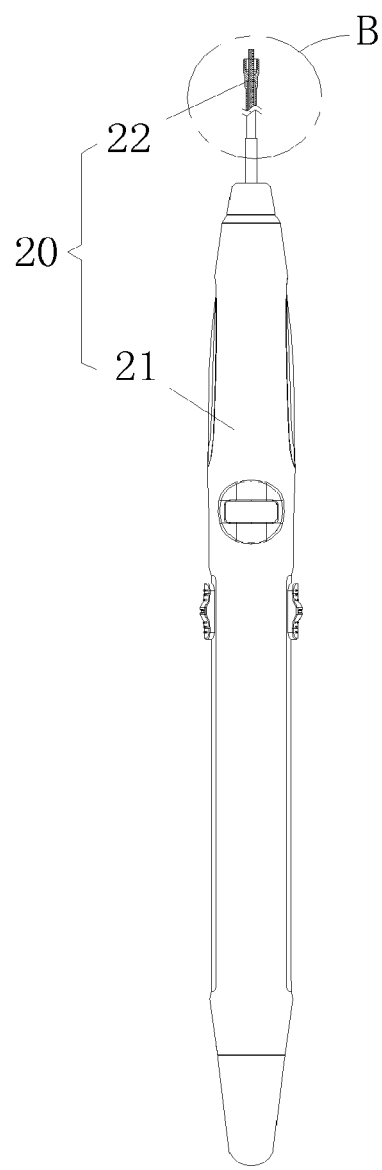
FIG. 3 is a structural schematic diagram of an occluder pushing device.
Figure 5A:
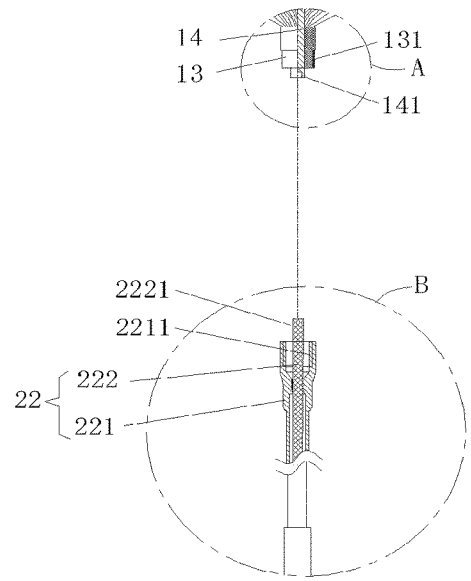
FIG. 5a is an enlarged structural assembly schematic diagram showing the portion in circle A in FIG. 2 and the portion in circle B in FIG. 3.

Referring also to FIGS. 2, 3, and 5a, in some embodiments, the occluder 10 includes a mesh disc 11, a flow blocking film 15, and a suturing part 16 for suturing the mesh disc 11 to the flow blocking film 15. To enable the distal end and the proximal end of the occluder 10 to be detachably connected with the distal ends of the pushing tube 221 and the traction element 222, respectively, a distal end plug head 12 and a proximal end bolt 13 are arranged at the distal end and the proximal end, respectively, of the occluder 10. The distal end plug head 12 is connected with an external thread 2221 of the traction element 222 through a locking element 14 with an internal thread 141, and the proximal end bolt 13 is provided with an external thread 131 that corresponds with the internal thread 2211 provided at the distal end of the pushing tube 221. Further, the connection with the occluder 10 may be removed or established by simply rotating the pushing tube 221 and the traction element 222 when releasing or recovering the occluder 10. Of course, it should be understood that, referring to FIG. 25, the proximal end bolt 13 is provided with a locking hole 132 through which the locking element 14 passes through and locks. The traction element 222 moves in the axial direction relative to the pushing tube 221 to enable the locking element 14 to drive the distal end plug head 12 to be close to or far away from the proximal end bolt 13 to unfold or fold the occluder 10.

It should be understood that, in other embodiments, the internal thread 141 may not be provided at the proximal end of the locking element 14, and the locking element 14 may be detachably connected with the traction element 222 by a buckle. In other words, the connection between the locking element 14 and the traction element 222 may be accomplished in other ways, which will not be specifically enumerated herein, so long as a detachable connection between the locking element 14 and the traction element 222 is ensured.

Figure 4:
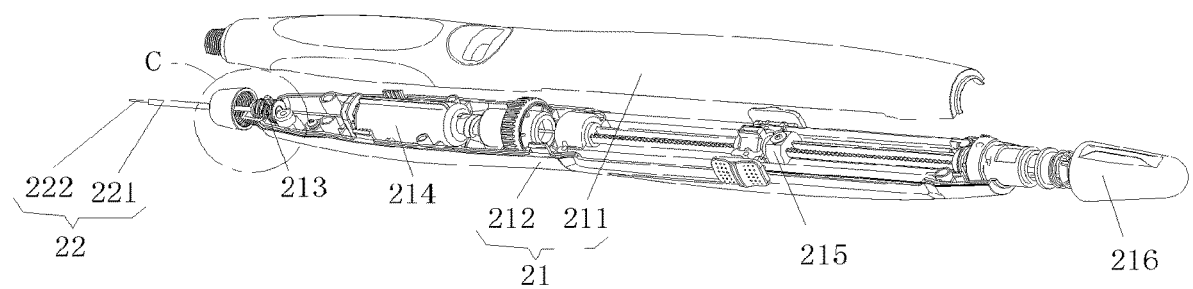
FIG. 4 is a schematic diagram of the internal structure of the pushing device shown in FIG. 3.
Figure 5B:
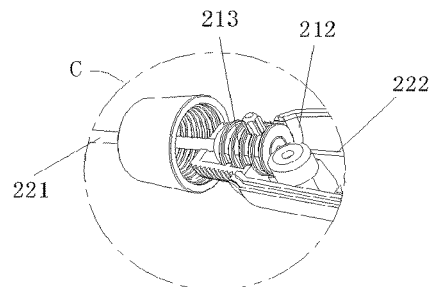
FIG. 5b is an enlarged structural diagram of the portion in circle C in FIG. 4.

Referring also to FIGS. 4 and 5b, in order to enable the traction element 222 to move within the pushing tube 221, a proximal end of the pushing tube 221 is mounted to a housing of the handle 21 through a fixing element 213. In order to facilitate the assembly of internal members of the handle 21, the housing of the handle 21 is formed by enclosing a cover 212 and a bottom housing 211. A corresponding fixing element 213 fixes the proximal end of the pushing tube 221 to the bottom housing 211 and enables the traction element 222 to pass through the pushing tube 221, a proximal end of the traction element 222 is connected to the translation mechanism 215, and the traction element 222 moves within the pushing tube 221 as driven by the translation mechanism 215. It should be understood that the proximal end of the traction element 222 passes through the proximal end of the pushing tube 221 to connect to the translation mechanism 215, and the locking component 214 connected to the traction element 222 can lock or release the traction element 222, thereby locking the relative positions between the traction element 222 and the pushing tube 221.

Figure 6:
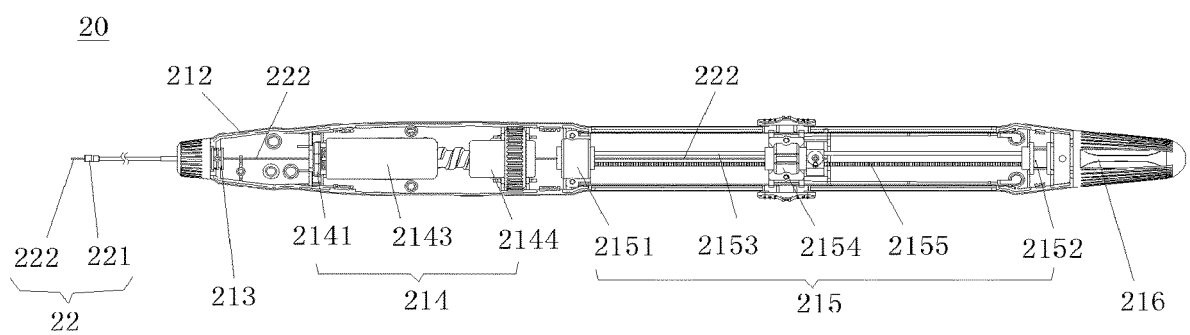
FIG. 6 is a top view of the internal structure of the pushing device shown in FIG. 4.
Figure 7:
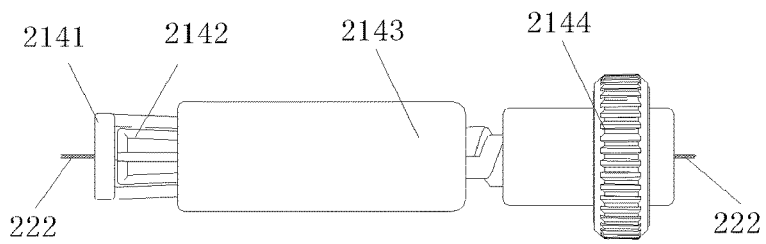
FIG. 7 is a structural diagram of a locking component shown in FIG. 6.
Figure 8:
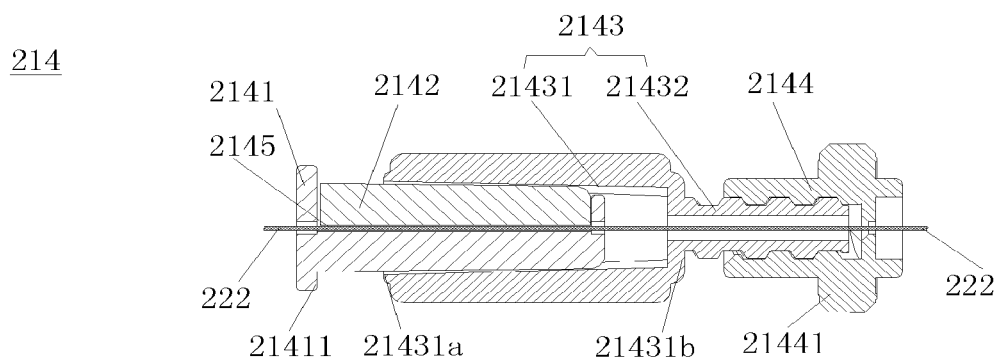
FIG. 8 is a sectional view of the locking component shown in FIG. 7.

Referring also to FIGS. 6-8, in some embodiments, the locking component 214 includes a fixing seat 2141, a movable element 2142, and an adjusting structure for adjusting a pore 2145 between the movable element 2142 and the fixing seat 2141. It should be understood that the adjusting structure may lock or release the traction element 222 by adjusting the size of the pore 2145 in such a manner that the movable element 2142 may clamp the fixing seat 2141 by pressing, or in such a manner that an annular element surrounding the movable element 2142 and the fixing seat 2141 may grip the movable element 2142 and the fixing seat 2141 when the annular element moves axially. The adjusting structure will be further described below with regard to how the gripping is accomplished.

Referring also to FIGS. 7 and 8, in some embodiments, the adjusting structure includes a sleeve 2143 surrounding the fixing seat 2141 and the movable element 2142, and a locking wheel 2144 that moves the sleeve 2143 axially relative to the fixing seat 2141 and the movable element 2142.

Specifically, the fixing seat 2141 is fixed in the handle 21 and the sleeve 2143 is connected with the locking wheel 2144 by threads. Thus, the rotation of the locking wheel 2144 may drive the sleeve 2143 to move axially to grip or release the fixing seat 2141 and the movable element 2142, thereby locking the traction element 222, and further locking or releasing the traction element 222 passing through the pore 2145 between the movable element 2142 and the fixing seat 2141. It should be understood that the diameter of the minimum inscribed circle of the projection of the sleeve 2143 on the cross section perpendicular to the axial direction is less than the diameter of the maximum circumscribed circle of the fixing seat 2141 and the movable element 2142; this ensures that a clamping force on the traction element 222 may be created by the gripping of the fixing seat 2141 and the movable element 2142 when the sleeve 2143 is moved axially relative to the fixing seat 2141 and the movable element 2142. Of course, this axial relative movement requires defining the axial relative positions of the locking wheel 2144 and the fixing seat 2141. Referring to FIG. 8, a radially outwardly formed side edge 21411 of the fixing seat 2141 axially limits the fixing seat 2141 to the bottom housing 212 of the handle 21. Similarly, the locking wheel 2144 is also axially limited to the bottom housing 212 of the handle 21, and to facilitate the operation of the locking wheel 2144, a hub 21441 of the locking wheel 2144 is at least partially exposed from the handle 21.

Continuing to refer to FIG. 8, in some embodiments, a tapered blind hole 21431 is formed in the sleeve 2143; a circular truncated cone is formed by the alignment of the movable element 2142 and the fixing seat 2141, and the circular truncated cone is positioned in the tapered blind hole 21431; an end 21431b that is far away from the opening 21431a of the tapered blind hole 21431 of the sleeve 2143 is threadably connected with the locking wheel 2144 through a screw 21432. The clamping or loosening between the fixing seat 2141 and the movable element 2142 is achieved when the tapered blind hole 21431 is close to or far away from the circular truncated cone, respectively. Of course, in the present embodiment, the threaded transmission by means of the screw 21432 is only to reduce the space occupied by the structure, and to facilitate the arrangement of the locking wheel 2144 having a larger diameter to improve the torsion-resistant performance. It should be understood that the sleeve 2143 may also be axially driven by directly matching the internal thread of the locking wheel 2144 with the external thread of the outer wall of the sleeve 2143.

Figure 9:
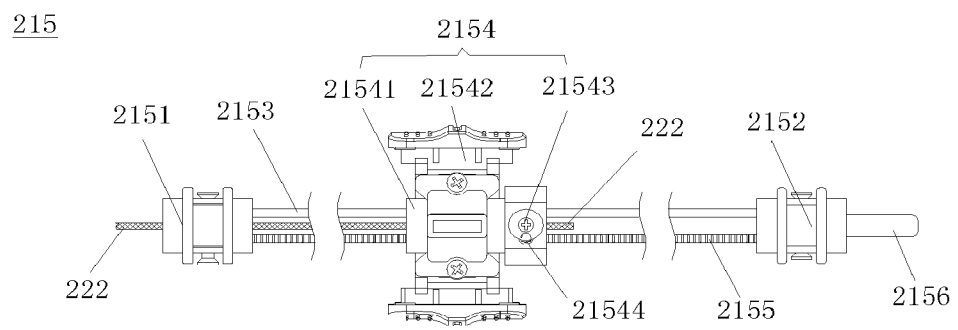
FIG. 9 is a structural diagram of a translation mechanism shown in FIG. 6.

Referring also to FIGS. 6 and 9, in some embodiments, the translation mechanism 215 includes a first rotating element 2151, a second rotating element 2152, a linear guide rail 2153, a balance sliding rail 2155, and a horizontal driving component 2154. The first rotating element 2151 is axially provided with a through hole 21541b through which the traction element 222 extends. The second rotating element 2152 is coaxial with the first rotating element 2151; and the linear guide rail 2153 and the balance sliding rail 2155 are provided on the first rotating element 2151 and the second rotating element 2152, respectively, in a manner of being parallel to a rotation axis of the first rotating element 2151. The proximal end of the traction element 222 passes through the through hole 21541b of the first rotating element 2151 and is fixed to the horizontal driving component 2154 so as to allow linear reciprocating motion along the linear guide rail 2153 and the balance sliding rail 2155 under the driving force of the horizontal driving component 2154, and then axially moves relative to the pushing tube 221 fixed to the handle 21 so as to fold or unfold the occluder 10.

Figure 13:
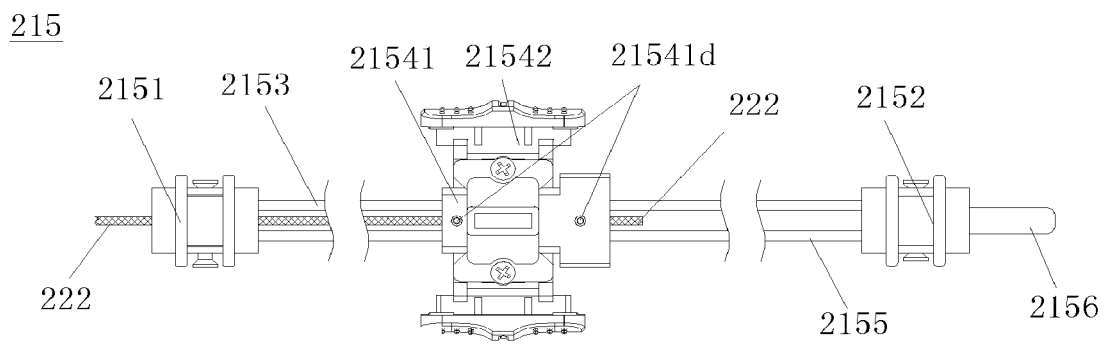
FIG. 13 is a connection schematic diagram of a traction element and a traction element mounting seat.
Figure 14:
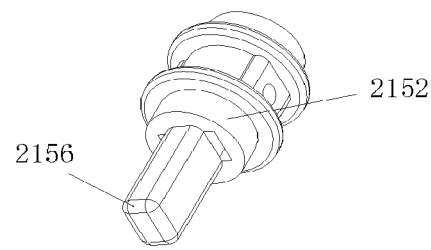
FIG. 14 is a structural diagram of a second rotating element.

Referring also to FIGS. 9 and 13, in some embodiments, the horizontal driving component 2154 includes a traction element mounting seat 21541 and a pushing part 21542 connected with the traction element mounting seat 21541. The traction element mounting seat 21541 is slidably provided on the linear guide rail 2153 and the balance sliding rail 2155, and the proximal end of the traction element 222 is fixed to the traction element mounting seat 21541. The pushing part 21542 is at least partially exposed from the handle 21 so as to push the traction element mounting seat 21541 to move along the linear guide rail 2153 and the balance sliding rail 2155. It should be understood that the traction element 222 may be fixed by a locking wire 21541d extending radially along the traction element mounting seat 21541, or may be fixed to the traction element mounting seat 21541 by other ways such as welding.

Figure 12:
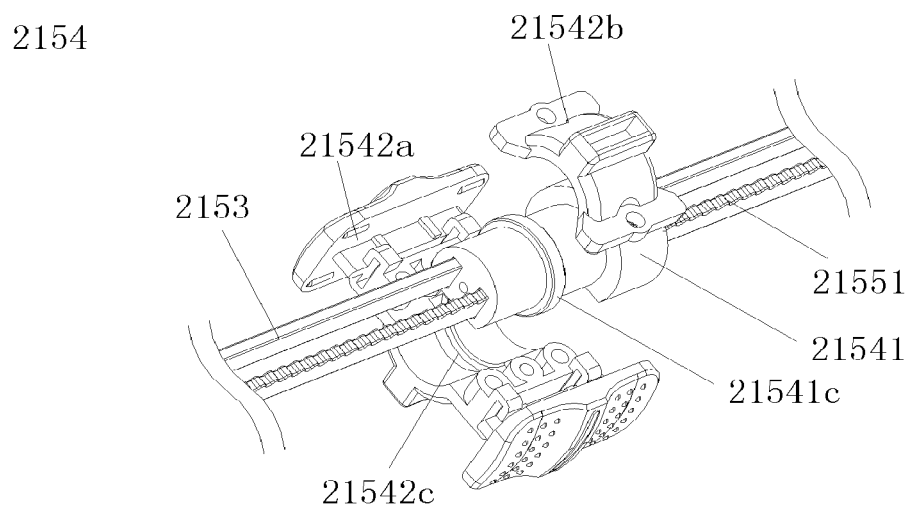
FIG. 12 is an exploded structural diagram of the horizontal driving component of the translation mechanism shown in FIG. 9.

Referring to FIG. 12, in some embodiments, in order to prevent the traction element mounting seat 21541 from pushing too fast without being blocked while pushing the traction element 222, damping edges 21551 are provided on the surface of the balance sliding rail 2155 along a moving direction of the traction element mounting seat 21541, and a sliding element 21545 which elastically abuts against the damping edges 21551 is provided in the traction element mounting seat 21541. Thus, when sliding axially, the traction element mounting seat 21541 will be blocked by the damping edges 21551 on the surface of the balance sliding rail 2155, so that the occluder 10 may be slowly released during the operation, thereby reducing the adverse impacts caused by pushing too fast.

Specifically, in order to maintain the sliding element 21545 in a state of elastically abutting against the damping edges 21551, an elastic element 21544 may be provided at an end of the sliding element 21545 far from the damping edges 21551, so as to urge the sliding element 21545 toward the damping edges 21551. It should be understood that a curved surface of the sliding element 21545 is usually used to abut against the damping edges 21551 so as to reduce wear during sliding, or to avoid inconvenience in pushing the traction element mounting seat 21541 caused by excessive blocking.

Figure 10:
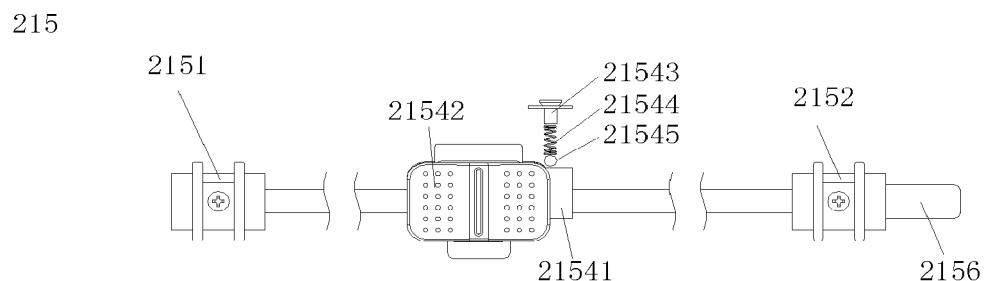
FIG. 10 is a bottom view of the translation mechanism shown in FIG. 9.
Figure 11:
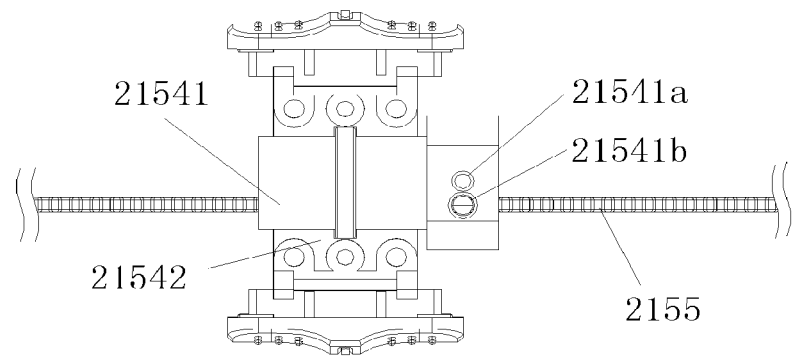
FIG. 11 is a structural diagram of a horizontal driving component of the translation mechanism shown in FIG. 9.

Referring also to FIGS. 10 and 11, in the above-described embodiments, the traction element mounting seat 21541 is radially formed with the through hole 21541b communicating with one sides of the damping edges 21551 to provide a mounting space for the elastic element 21544 and the sliding element 21545. The elastic element 21544 is a spring, and the sliding element 21545 is a ball. The bottom of the spring is pressed against the ball to enable the ball to abut against the damping edges 21551, and the top of the spring is radially limited along the traction element mounting seat 21541 through a fastening element 21543. It should be understood that the fastening element 21543 is a grub screw mounted on one side of the through hole 21541b, and correspondingly, a threaded hole 21541a is formed in the traction element mounting seat 21541 to cooperate with the grub screw to fasten and press the spring downwardly.

In some embodiments, the pushing part 21542 is axially limited on the traction element mounting seat 21541, and the first rotating element 2151 and the second rotating element 2152 drive the traction element mounting seat 21541 to rotate around the rotation axis of the first rotating element 2151 relative to the pushing part 21542 through the linear guide rail 2153 and the balance sliding rail 2155. The traction element mounting seat 21541 drives the traction element 222 to rotate axially within the pushing tube 221, thereby connecting or separating the traction element with or from the locking element 14 of the occluder 10.

In some embodiments, the traction element mounting seat 21541 and the pushing part 21542 are axially limited by a limiting edge 21541c and a limiting groove 21542c, which are mutually aligned circumferentially, and the cross section of the limiting edge 21541c and the limiting groove 21542c at the aligned position is circular to allow for the rotation of the traction element mounting seat 21541 relative to the pushing part 21542. It should be understood that the limiting edge 21541c may be provided on the traction element mounting seat 21541 or on the pushing part 21542. When the limiting edge 21541c is provided on the traction element mounting seat 21541, the pushing part 21542 is provided with the limiting groove 21542c aligned with the limiting edge 21541c; and when the limiting edge 21541c is provided on the pushing part 21542, the traction element 222 is provided with the limiting groove 21542c aligned with the limiting edge 21541c. In the present embodiment, as shown in FIG. 12, the traction element mounting seat 21541 and the pushing part 21542 are each provided with the limiting edge 21541c and the limiting groove 21542c which are aligned with each other, and it should be understood that the pushing part 21542 includes a pushing part seat 21542a and a pushing part upper cover 21542b to facilitate the assembly of the pushing part 21542 on the traction element mounting seat 21541.

In some embodiments, to facilitate the rotation of the traction element mounting seat 21541 relative to the pushing part 21542, a rotation mechanism 216 is provided at an end of the second rotating element 2152 far from the first rotating element 2151. The rotation mechanism 216 is rotated to drive the second rotating element 2152 to rotate, thereby driving the traction element mounting seat 21541 to rotate axially through the linear guide rail 2153 and the balance sliding rail 2155.

Figure 15:
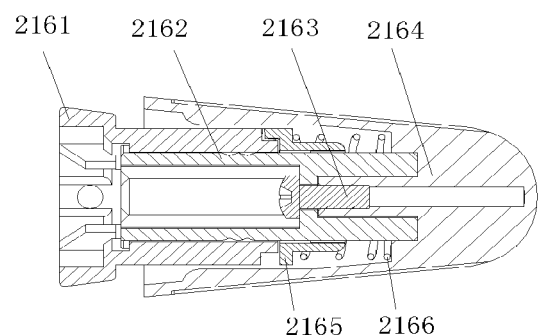
FIG. 15 is an axial sectional view of a rotation mechanism.

Specifically, referring to FIG. 15, in some embodiments, the rotation mechanism 216 includes a base 2161 and an adjusting rod 2162. The base 2161 is a hollow barrel and is fixed to the housing of the handle 21; the adjusting rod 2162 is slidably inserted into the base 2161 and rotatably linked with the second rotating element 2152. Thus, the adjusting rod 2162 may rotate within the base 2161 to rotate in linkage with the second rotating element 2152. Referring also to FIGS. 14 and 18-20, it should be understood that the second rotating element 2152 is inserted through a rotating shaft control rod 2156 into a slot 21625 formed axially along the adjusting rod 2162, and the cross section perpendicular to the axis is non-circular, i.e., the slot 21625 allows the rotating shaft control rod 2156 to move axially while limiting only the rotational degree of freedom of the rotating shaft control rod 2156 to achieve rotational linkage around the axis.

In some embodiments, the locking structure is provided on the base 2161 and the adjusting rod 2162. The locking structure has a locking state and an unlocking state in which the rotational degree of freedom of the adjusting rod 2162 within the base 2161 is respectively restrained or released;

and the locking structure may be in the locking state or the unlocking state by axially adjusting the relative positions of the adjusting rod 2162 and the base 2161. Thus, rotation of the second rotating member 2152 due to accidentally touching of the adjusting rod 2162 during the pushing of the occluder 10 is prevented. The distal end of the traction element 222 fixedly connected to the traction element mounting seat 21541 is detached from the fastening element of the occluder 10 by rotating the second rotating member 2152, and if the second rotating member 2152 is accidentally rotated, it would cause the occluder 10 to be accidentally released. Therefore, if the rotation of the second rotating member 2152 is prevented, accidental release of the occluder 10 can be prevented.

Figure 16:
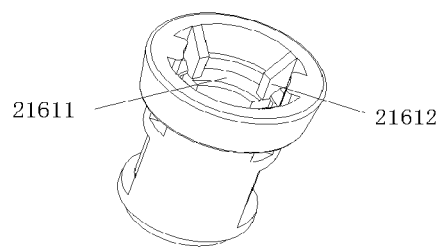
FIG. 16 is a structural diagram of a base of the rotation mechanism.
Figure 17:
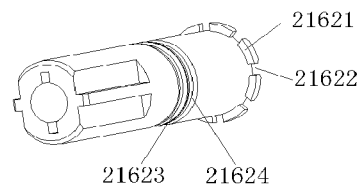
FIG. 17 is a structural diagram of an adjusting rod of the rotation mechanism.
Figure 18:
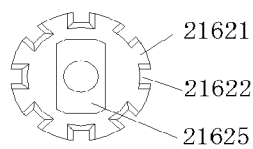
FIG. 18 is an end view, close to the second rotating element, of the adjusting rod shown in FIG. 17.

Referring also to FIGS. 16-18, in some embodiments, the locking structure includes stopping pieces 21612, stopping teeth 21621 and an annular groove 21611. The stopping pieces 21612 are provided circumferentially at intervals around an inner side wall of the base 2161; the stopping teeth 21621 are provided circumferentially at intervals around an outer side wall of the adjusting rod 2162, and tooth grooves 21622 are formed between adjacent stopping teeth 21621. The annular groove 21611 is provided circumferentially around the inner side wall of the base 2161. When the adjusting rod 2162 is rotated within the base 2161, the stopping teeth 21621 may rotate within the annular groove 21611. The stopping pieces 21612 may be clamped in the tooth grooves 21622 or the stopping teeth 21621 may be moved into the annular groove 21611 by axially adjusting the relative positions of the adjusting rod 2162 and the base 2161 to limit or release the rotational degree of freedom between the adjusting rod 2162 and the base 2161. It should be understood that when the rotational degree of freedom between the adjusting rod 2162 and the base 2161 is limited, even if the adjusting rod 2162 is touched accidently, the adjusting rod 2162 will not rotate axially, thereby avoiding accidental touching of the pushing device 20 causing the traction element 222 to rotate to be disconnected from the occluder 10, and ensuring the accuracy of the release of the occluder 10.

In some embodiments, position clamping structures are provided on the inner side wall of the base 2161 and the outer side wall of the adjusting rod 2162, so that the adjusting rod 2162 may be axially limited in the base 2161 without interference by external forces. Further, the adjusting rod 2162 and the base 2161 are kept in a locked or released state of the rotational degree of freedom, so that accidental touching resulting in the adjusting rod 2162 being unlocked from the rotational degree of freedom of the base 2161 is avoided.

Figure 19:
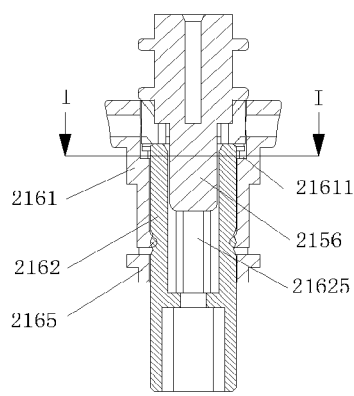
FIG. 19 is an assembly schematic diagram of the second rotating element, the adjusting rod and the base.
Figure 20:
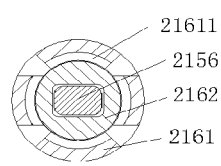
FIG. 20 is a sectional view taken along a section line I-I in FIG. 19.
Figure 21:
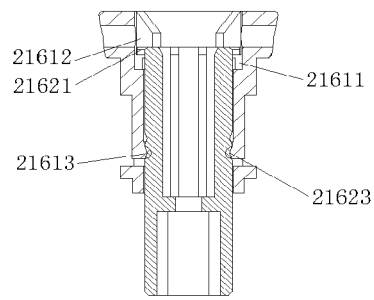
FIG. 21 is a state diagram showing the adjusting rod being axially rotatable relative to the base.

Referring also to FIGS. 15, 17, and 19, in some embodiments, the rotation mechanism 216 further includes a rotary cover 2164, a spring seat 2165, and a spring 2166 elastically pressed between the spring seat 2165 and the rotary cover 2164. The rotary cover 2164 is fixed at an end of the adjusting rod 2162 far away from the second rotating element 2152; and the spring seat 2165 surrounds the base 2161. The rotary cover 2164 may be fixedly connected with the adjusting rod 2162 through a tightening screw 2163, and of course the fixing may also be accomplished through a buckle or the like. In this embodiment, as combined with FIG. 21, the position clamping structure includes a clamping ring 21613 and a first clamping groove 21623. The clamping ring 21613 extends radially from the inner side wall of the base 2161 and abuts against the outer side wall of the adjusting rod 2162; the first clamping groove 21623 is circumferentially formed around the outer side wall of the adjusting rod 2162; and when the clamping ring 21613 is received inside the first clamping groove 21623, the stopping pieces 21612 are clamped in the tooth grooves 21622. Thus the adjusting rod 2162 is axially maintained with the base 2161 in a state where the rotational degree of freedom is locked under the limitation of the clamping ring 21613 and the first clamping groove 21623, i.e., the adjusting rod 2162 cannot rotate relative to the base 2161, so as to prevent the traction element 222 from rotating due to accidental touching. When the clamping ring 21613 and the first clamping groove 21623 are disengaged, the stopping groove in the adjusting rod 2162 is driven away from the stopping pieces 21612 and located in the annular groove 21611 under the elastic force of the spring 2166, so that by rotating the rotary cover 2164 to rotate the traction element 222, the occluder 10 may be released through the disengagement from the connection, or may be recovered through the establishment of the connection.

Figure 22:
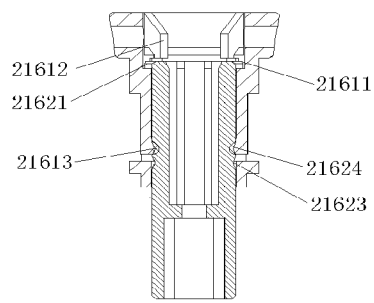
FIG. 22 is a state diagram showing an adjusting rod being axially limited to the base.

Preferably, as combined with FIG. 22, the position clamping structure further includes a second clamping groove 21624, wherein the second clamping groove 21624 is circumferentially formed around the outer side wall of the adjusting rod 2162; and when the clamping ring 21613 is received inside the second clamping groove 21624, the stopping teeth 21621 are positioned in the annular groove 21611. The alignment of the second clamping groove 21624 and the clamping ring 21613 maintains the adjusting rod 2162 and the base 2161 in the released state of the rotational degree of freedom, thereby avoiding the situation that the rotational degree of freedom of the adjusting rod 2162 is not sufficiently maintained in the released state when the spring 2166 fails, thereby improving the safety of operation, and ensuring that no traction element 222 will rotate and be disengaged from the occluder 10 due to accidental touching of the pushing device 20.

Figure 25:
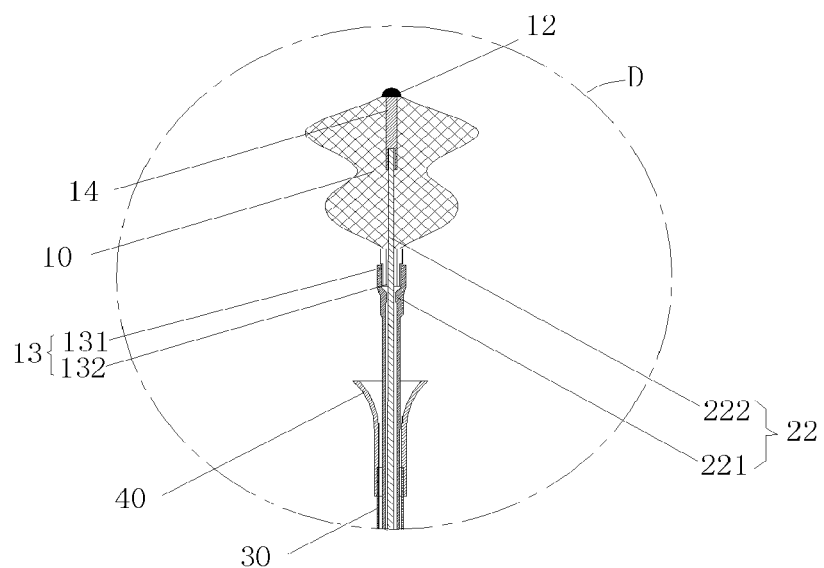
FIG. 25 is an enlarged structural view of the portion in circle D of FIG. 24.
Figure 26:
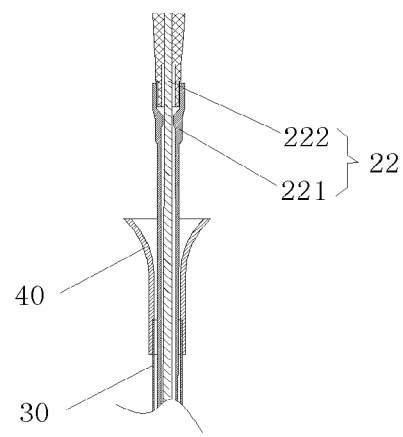
FIG. 26 is another state diagram of the occluder during the operation of the pushing device (when the occluder is fully folded)
Figure 27:
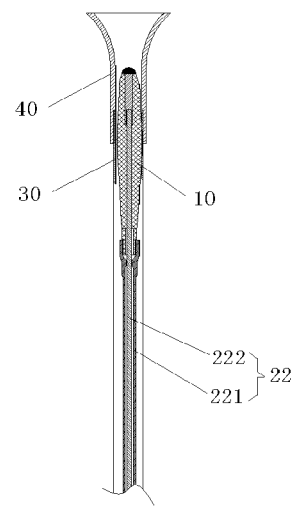
FIG. 27 is a schematic diagram showing a pushing component being pulled to a proximal end to advance the occluder into the guide sheath through the preloader.
Figure 28:
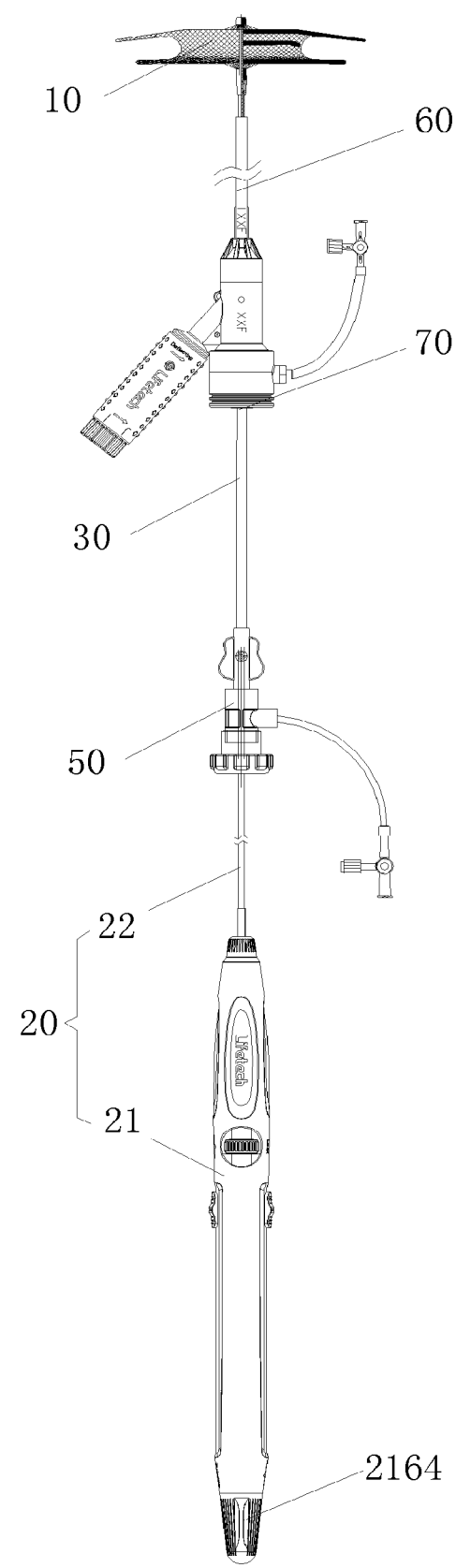
FIG. 28 is a schematic diagram of a pushing device pushing out the occluder through the delivery sheath after the occluder passes through a hemostatic valve and the guide sheath when the guide sheath is connected with the delivery sheath.

Referring also to FIGS. 24 and 25, when the pushing device 20 is used to deploy the occlude 10, the pushing component 22 connected with the handle 21 sequentially passes through the hemostatic valve 50, the guide sheath 30 and the preloader 40, and the pushing tube 221 and the traction element 222 of the pushing component 22 are connected with the proximal end bolt 13 and the locking element 14 of the occluder 10, respectively. Thus, the traction element 222 may be controlled to move toward the distal end along the pushing tube 221 by pushing the pushing part 21542 on the handle 21 to move toward the distal end, leading the fastening element to drive the distal end plugging head 12 away from the proximal end bolt 13 to stretch and shape the occluder 10 axially. With continued pushing on the pushing part 21542 toward the distal end, the occluder 10 is fully folded as shown in FIG. 26, and the hub 21441 of the locking wheel 2144 on the handle 21 is rotated to lock the relative positions between the traction element 222 and the pushing tube 221, so as to maintain the occluder 10 in the folded state. Referring to FIG. 27, pulling the pushing component 22 toward the proximal end may move the occluder 10 into the guide sheath 30 through the preloader 40. The preloader 40 is removed from the guide sheath 30 and the distal end of the guide sheath 30 is connected with the proximal end of the delivery sheath 60, so that the operation of loading the occluder 10 into the occluder delivery system is completed. Referring to FIG. 28, the occluder 10 is pushed by the occluder delivery system through the delivery sheath 60 to a pre-determined position where the occluder 10 will be unfolded and released. It should be understood that since the movement of the traction element 222 in the push tube 221 is reversibly controlled by the pushing device 20, i.e., after unlocking the traction element 222 from the locking component 214, the pushing part 21542 is pushed toward the proximal end to allow the traction element 222 to drive the locking wire to be close to the proximal end bolt 13 connected with the distal end of the pushing tube 221, and then the occluder 10 may be adjusted from the folded state to the unfolded state. In the process of adjusting the state of the occluder 10 by the pushing device 20, when the traction element mounting seat 21541 slides axially, the traction element mounting seat 21541 will be blocked by the damping edges 21551 on the surface of the balance sliding rail 2155, so that the occluder 10 may be slowly released during the operation, thereby reducing the adverse impacts caused by pushing too quickly.

The various technical features of the above-mentioned embodiments may be combined in any combination, and in order to simplify the description, not all possible combinations of the various technical features of the above-described embodiments are described, however, as long as there is no conflict between these technical features, they should be all considered to be the scope of disclosure contained in this description.

The above embodiments are merely illustrative of several implementations of the present disclosure, which are described in more detail and are not to be construed as limiting the scope of the disclosure. It should be noted that several variations and modifications may be made by those skilled in the art without departing from the spirit of the disclosure, which all fall within the scope of the disclosure. Therefore, the protection scope of the disclosure shall be determined by the appended claims.

The invention claimed is:

1. An occluder pushing device, comprising:
a pushing component comprising a pushing tube and a traction element slidably inserted into the pushing tube; and
a handle fixedly connected with a proximal end of the pushing tube and internally provided with a translation mechanism and a rotation mechanism; wherein the translation mechanism is configured to drive the traction element to move in an axial direction within the pushing tube; the rotation mechanism is configured to drive the traction element to rotate around an axis within the pushing tube;
the rotation mechanism comprises a locking structure for locking or releasing linkage between the rotation mechanism and the traction element.

2. The occluder pushing device of claim 1, wherein the translation mechanism comprises:
a first rotating element axially provided with a through hole through which the traction element extends;
a second rotating element coaxial with the first rotating element;
a linear guide rail and a balance sliding rail respectively provided on the first rotating element and the second rotating element and being parallel to a rotation axis of the first rotating element; and
a horizontal driving component configured to drive a proximal end of the traction element to generate linear reciprocating motion along the linear guide rail and the balance sliding rail.

3. The occluder pushing device of claim 2, wherein the horizontal driving component comprises:
a traction element mounting seat slidably provided on the linear guide rail and the balance sliding rail, wherein the proximal end of the traction element is fixed to the traction element mounting seat; and
a pushing part connected with the traction element mounting seat and at least partially exposed from the handle so as to push the traction element mounting seat to move along the linear guide rail and the balance sliding rail.

4. The occluder pushing device of claim 3, wherein a damping edge is provided on a surface of the balance sliding rail along a moving direction of the traction element mounting seat, and a sliding element which elastically abuts against the damping edge is provided in the traction element mounting seat.

5. The occluder pushing device of claim 3, wherein the pushing part is axially limited on the traction element mounting seat, and the first rotating element and the second rotating element transmit the traction element mounting seat to rotate around the rotation axis of the first rotating element relative to the pushing part through the linear guide rail and the balance sliding rail.

6. The occluder pushing device of claim 5, wherein the traction element mounting seat and the pushing part are axially limited through a limiting edge and a limiting groove which are mutually aligned circumferentially, and the cross section of the limiting edge and the limiting groove at the matching position are circular to achieve the rotation of the traction element mounting seat relative to the pushing part.

7. The occluder pushing device of claim 2, wherein the rotation mechanism is provided at an end of the second rotating element far from the first rotating element, and the rotation mechanism further comprises:
a base, which is a hollow barrel and is fixed to a housing of the handle; and
an adjusting rod slidably inserted into the base and rotatably linked with the second rotating element, wherein the locking structure is provided on the base and the adjusting rod, and has a locked state and an unlocked state to respectively restrain and release the rotational degree of freedom of the adjusting rod within the base; and
wherein the locking structure is capable of being placed in the locked state or the unlocked state by axially adjusting relative positions of the adjusting rod and the base.

8. The occluder pushing device of claim 7, wherein the locking structure comprises:
stopping pieces circumferentially provided at intervals around an inner side wall of the base;
stopping teeth circumferentially provided at intervals around an outer side wall of the adjusting rod, wherein tooth grooves are formed between the adjacent stopping teeth; and
an annular groove circumferentially formed around the inner side wall of the base, wherein when the adjusting rod rotates within the base, the stopping teeth rotate in the annular groove; and
wherein the stopping pieces are capable of being clamped in the tooth grooves or the stopping teeth are capable of being moved into the annular groove by axially adjusting the relative positions of the adjusting rod and the base.

9. The occluder pushing device of claim 8, wherein position clamping structures are provided on the inner side wall of the base and the outer side wall of the adjusting rod, so that the adjusting rod is axially limited in the base without interference of external force.

10. The occluder pushing device of claim 9, wherein the rotation mechanism further comprises:
a rotary cover fixed at an end of the adjusting rod far from the second rotating element;

a spring seat surrounding the base; and
a spring elastically pressed between the spring seat and the rotary cover; and
wherein the position clamping structure comprises a clamping ring and a first clamping groove, wherein the clamping ring extends radially from the inner side wall of the base and abuts against the outer side wall of the adjusting rod; the first clamping groove is circumferentially formed around the outer side wall of the adjusting rod; and
when the clamping ring is buckled with the first clamping groove, the stopping pieces are clamped in the tooth grooves.

11. The occluder pushing device of claim 10, wherein the position clamping structure further comprises a second clamping groove, wherein the second clamping groove is circumferentially formed around the outer side wall of the adjusting rod; and
when the clamping ring is buckled with the second clamping groove, the stopping teeth are positioned in the annular groove.

12. The occluder pushing device of claim 1, wherein the handle comprises a housing, the handle internally provided with a locking component, the locking component being received in housing, and being configured to lock relative positions of the traction element and the pushing tube.

13. The occluder pushing device of claim 12, wherein the locking component comprises:
a fixing seat fixed in the handle;
a movable element, a pore is formed between the movable element and the fixing seat for the traction element to pass through; and
an adjusting structure configured to adjust the pore between the movable element and the fixing seat so as to lock or release the traction element.

14. The occluder pushing device of claim 13, wherein the adjusting structure comprises:
a sleeve surrounding the fixing seat and the movable element, wherein the diameter of the minimum inscribed circle of the projection of the sleeve on the cross section perpendicular to the axial direction is less than the diameter of the maximum circumscribed circle of the fixing seat and the movable element; and
a locking wheel axially limited in the handle and in threaded connection with the sleeve, wherein a hub of the locking wheel is at least partially exposed from the handle to rotate the locking wheel to transmit the sleeve to move axially, so that the sleeve grips or releases the fixing seat and the movable element.

15. The occluder pushing device of claim 14, wherein a tapered blind hole is formed in the sleeve; a circular truncated cone is formed by the alignment of the movable element and the fixing seat, and positioned in the tapered blind hole; and an end of the sleeve far from the opening of the tapered blind hole is in threaded connection with the locking wheel through a screw.

16. An occluder delivery system, comprising the occluder pushing device of claim 1, and
a delivery sheath, which is a hollow tube, and the pushing tube of the occluder pushing device is slidably inserted into the delivery sheath; and
a sheath core connected to a proximal end of the delivery sheath and configured to adjust a bending direction of the delivery sheath so that the pushing tube pushes the occluder to a defect to be occluded along the delivery sheath.

17. The occluder delivery system of claim 16, wherein the delivery system further comprises a hemostatic valve, wherein a hollow guide sheath is detachably connected between the delivery sheath and the hemostatic valve, and an inner cavity of the guide sheath is communicated with an inner cavity of the delivery sheath and an inner cavity of the hemostatic valve.

18. The occluder delivery system of claim 17, wherein the delivery system further comprises a preloader detachably connected to a distal end of the guide sheath, and the preloader comprises a horn section and an interface section, and a connecting section connected between the horn section and the interface section.

19. An occluder pushing device, comprising:
a pushing component comprising a pushing tube and a traction element slidably inserted into the pushing tube; and
a handle fixedly connected with a proximal end of the pushing tube and internally provided with a locking component, a translation mechanism and a rotation mechanism; wherein the translation mechanism is configured to drive the traction element to move in an axial direction within the pushing tube; the rotation mechanism is configured to drive the traction element to rotate around an axis within the pushing tube;
the locking component is configured to lock relative positions of the traction element and the pushing tube.

20. The occluder pushing device of claim 19, wherein the locking component comprises:
a fixing seat fixed in the handle;
a movable element, a pore is formed between the movable element and the fixing seat for the traction element to pass through; and
an adjusting structure configured to adjust the pore between the movable element and the fixing seat so as to lock or release the traction element;
wherein the adjusting structure comprises:
a sleeve surrounding the fixing seat and the movable element, wherein the diameter of the minimum inscribed circle of the projection of the sleeve on the cross section perpendicular to the axial direction is less than the diameter of the maximum circumscribed circle of the fixing seat and the movable element; and
a locking wheel axially limited in the handle and in threaded connection with the sleeve, wherein a hub of the locking wheel is at least partially exposed from the handle to rotate the locking wheel to transmit the sleeve to move axially, so that the sleeve grips or releases the fixing seat and the movable element;
wherein a tapered blind hole is formed in the sleeve; a circular truncated cone is formed by the alignment of the movable element and the fixing seat, and positioned in the tapered blind hole; and an end of the sleeve far from the opening of the tapered blind hole is in threaded connection with the locking wheel through a screw.

* * * * *